United States Patent [19]

Nesvadba et al.

[11] Patent Number: 5,216,052

[45] Date of Patent: Jun. 1, 1993

[54] BISBENZOFURAN-2-ONES

[75] Inventors: Peter Nesvadba, Marly; Carla Attinger-Sorato, Basel, both of Switzerland

[73] Assignee: Ciba-Geigy Corporation, Ardsley, N.Y.

[21] Appl. No.: 903,646

[22] Filed: Jun. 24, 1992

[30] Foreign Application Priority Data

Jul. 1, 1991 [CH] Switzerland .......... 1935/91

[51] Int. Cl.$^5$ .......... C08K 5/15; C07D 493/00
[52] U.S. Cl. .......... 524/108; 106/176; 523/455; 523/511; 524/109; 549/305; 549/307
[58] Field of Search .......... 549/305, 307; 524/108, 524/109; 523/455, 511; 106/176

[56] References Cited

U.S. PATENT DOCUMENTS 4,190,583  2/1980  Bauer et al. .......... 260/340.5
4,338,244  7/1982  Hinsken et al. .......... 524/109

FOREIGN PATENT DOCUMENTS 0146269  6/1985  European Pat. Off. .
0182507  5/1986  European Pat. Off. .
2754490  6/1979  Fed. Rep. of Germany .
2944295  5/1980  Fed. Rep. of Germany .
61-138648 6/1986  Japan .
2034308  6/1980  United Kingdom .

OTHER PUBLICATIONS

J. Chem. Soc. 1956, 1622.
Organic Syntheses Collective vol. 3 p. 326.
Houben-Weyl vol. 6/IC, 1030.
Organkem 1986, 402–408.

*Primary Examiner*—Veronica P. Hoke
*Attorney, Agent, or Firm*—Luther A. R. Hall

[57] ABSTRACT

Compounds of formula I

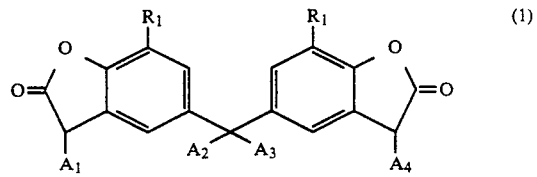

wherein $R_1$ is hydrogen, $C_1$–$C_8$alkyl, $C_5$–$C_8$cycloalkyl or $C_7$–$C_9$phenylalkyl, $A_1$ and $A_4$ are phenyl,

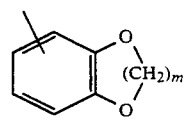

or phenyl which is substituted by 1 to 3 radicals $R_3$, which radicals $R_3$ are each independently of one another selected from the group consisting of $C_1$–$C_4$alkyl, $C_1$–$C_{18}$alkoxy, $C_3$–$C_4$alkenyloxy, $C_7$–$C_9$phenylalkoxy, $C_5$–$C_8$cycloalkoxy, $C_1$–$C_{18}$alkanoyloxy, $C_3$–$C_{18}$alkenyloxy, benzoyloxy, phenoxy and hydroxy, m is 1 or 2, $A_2$ and $A_3$, together with the linking carbon atom, form a $C_5$–$C_7$cycloalkylidene ring which is unsubstituted or substituted by 1 to 3 $C_1$–$C_4$alkyl groups, are very suitable for stabilising organic materials against thermal, oxidative or light-induced degradation.

13 Claims, No Drawings

BISBENZOFURAN-2-ONES

The present invention relates to novel bisbenzofuran-2-ones, to a process for their preparation, to the use of these compounds for stabilising organic materials and to the stabilised organic material thereby obtained.

Bisbenzofuran-2-ones are disclosed, inter alia, in U.S. Pat. No. 4,338,244. This patent specification also describes the use of these compounds for stabilising organic materials.

The invention provides compounds of formula (1)

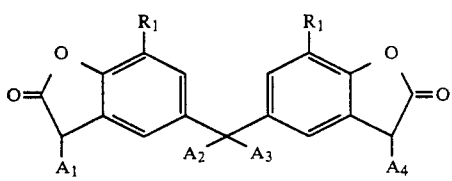

wherein $R_1$ is hydrogen, $C_1$-$C_8$alkyl, $C_5$-$C_8$cycloalkyl or $C_7$-$C_9$phenylalkyl, $A_1$ and $A_4$ are phenyl,

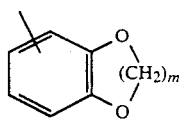

or phenyl which is substituted by 1 to 3 radicals $R_3$, which radicals $R_3$ are each independently of one another selected from the group consisting of $C_1$-$C_4$alkyl, $C_1$-$C_{18}$alkoxy, $C_3$-$C_4$alkenyloxy, $C_7$-$C_9$phenylalkoxy, $C_5$-$C_8$cycloalkoxy, $C_1$-$C_{18}$alkanoyloxy, $C_3$-$C_{18}$alkenoyloxy, benzoyloxy, phenoxy and hydroxy, m is 1 or 2, $A_2$ and $A_3$, together with the linking carbon atom, form a $C_5$-$C_7$cycloalkylidene ring which is unsubstituted or substituted by 1 or 3 $C_1$-$C_4$alkyl groups.

$C_1$-$C_8$Alkyl is a branched or unbranched radical and may typically be methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl or 2-ethylhexyl. A preferred meaning of $R_1$ is tert-butyl.

$C_5$-$C_8$Cycloalkyl may typically be cyclopentyl, cyclohexyl, cycloheptyl or cyclooctyl. A preferred meaning of $R_1$ is cyclohexyl.

$C_7$-$C_9$Phenylalkyl may typically be benzyl, α-methylbenzyl, α,α-dimethylbenzyl or 2-phenylethyl. Benzyl is preferred.

$C_1$-$C_{18}$Alkoxy may typically be methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

$C_3$-$C_4$Alkenyloxy may typically be —O—CH$_2$—CH=CH$_2$ or —O—CH$_2$—CH=CH—CH$_3$.

$C_7$-$C_9$Phenylalkoxy may typically be benzoxy, α-methylbenzoxy, α,α-dimethylbenzoxy or 2-phenylethoxy. Benzoxy is preferred.

$C_5$-$C_8$Cycloalkoxy may typically be cyclopentoxy, cyclohexoxy, cycloheptoxy or cyclooctoxy. Cyclopentoxy and cyclohexoxy are particularly preferred.

$C_1$-$C_{18}$Alkanoyloxy may typically be formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy or octadecanoyloxy.

$C_3$-$C_{18}$Alkenoyloxy may typically be propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, iso-dodecenoyloxy, oleoyloxy, n-2-octadecenoyloxy or n-4-octadecenoyloxy.

A preferred object of the invention is the provision of compounds of formula (1), wherein $R_1$ is hydrogen, $C_1$-$C_8$alkyl or $C_5$-$C_8$cycloalkyl, $A_1$ and $A_4$ are phenyl, $A_2$ and $A_3$ together form a group

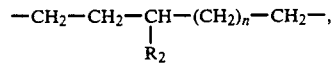

wherein, if n is 1, $R_2$ is hydrogen or $C_1$-$C_4$alkyl, and, if n is 0 or 2, $R_2$ is hydrogen.

A further preferred object of the invention is the provision of compounds of formula (1), wherein $R_1$ is hydrogen, $C_1$-$C_4$alkyl or cyclohexyl.

Particularly preferred compounds of formula (1) are those wherein $R_1$ is tert-butyl and $A_2$ and $A_3$ together are a group

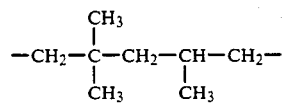

or

More particularly it is an object of the invention to provide compounds of formula (1), wherein $A_1$ and $A_4$ are phenyl or phenyl which is substituted by 1 to 3 radicals $R_3$, which radicals $R_3$ are each independently of one another selected from the group consisting of $C_1$-$C_4$alkyl, $C_1$-$C_{18}$alkoxy, benzoxy, $C_1$-$C_{18}$alkanoyloxy, benzoyloxy and hydroxy.

Also preferred are compounds of formula (1), wherein $A_1$ and $A_4$ are

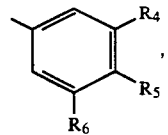

wherein $R_4$ and $R_6$ are each independently of the other hydrogen or $C_1$-$C_4$alkyl, and $R_5$ is hydroxy, $C_1$-$C_{18}$alkoxy, $C_1$-$C_{18}$alkanoyloxy or benzoxy.

More especially preferred compounds of formula (1) are those wherein $R_1$ is hydrogen, $C_1$-$C_4$alkyl or cyclohexyl, $A_1$ and $A_4$ are phenyl,

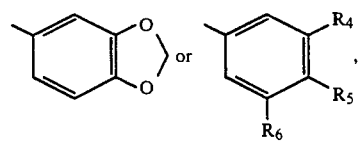

wherein $R_4$ and $R_6$ are each independently of the other hydrogen or methyl, and $R_5$ is hydroxy, $C_1$-$C_{18}$alkoxy, methyl, $C_1$-$C_8$alkanoyloxy or benzoxy, $A_2$ and $A_3$, together with the linking carbon atom, form a $C_5$-$C_7$cycloalkylidene ring, or $A_2$ and $A_3$ together are a group

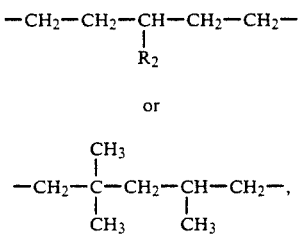

wherein $R_2$ is methyl or tert-butyl.

The novel compounds may be prepared in a manner known per se, conveniently and preferably by reacting a bisphenol of formula (2)

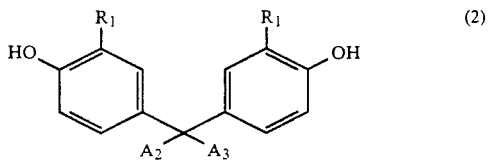

wherein $R_1$, $A_2$ and $A_3$ are as previously defined, with mandelic acid or mandelic acid which is substituted at the phenyl ring, at elevated temperature, preferably in the range from 160° to 200° C. This process is disclosed in U.S. Pat. No. 4,338,244.

The mandelic acids which are substituted at the phenyl ring are known from the literature and can be prepared conveniently in accordance with J. Chem. Soc. 1956, 1622, Organic Synthesis Coll. Vol. III, page 326, or with EP-A-182 507, EP-A-146 269, DE 2 944 295 or DE 2 754 490.

When using a mandelic acid substituted at the phenyl ring by hydroxy, the reaction is carried out in a solvent such as acetic acid in the temperature range from 50°-130° C., preferably from 60°-80° C.

The esterification of the phenolic group is carried out by known conventional esterification methods as described in Organikum 1986, pages 402–408, typically by acylation of an acid chloride.

Bisphenols of formula (2) can be prepared in accordance with Houben-Weyl, Methoden der organischen Chemie, Vol. 6/1c, 1030.

The novel compounds are suitable for stabilising organic materials against thermal, oxidative or light-induced degradation.

Illustrative examples of such materials are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which may be crosslinked), for example high density polyethylene (HDPE), low density polyethylene (LDPE), linear low density polyethylene (LLDPE), branched low density polyethylene (BLDPE).

2. Mixtures of the polymers mentioned in 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene, linear low density polyethylene (LLDPE) and its mixtures with low density polyethylene (LDPE), propylen/butene-1, ethylene/hexene, ethylene/ethylpentene, ethylene/heptene, ethylene/octene, propylene/isobutylene, ethylene/but-1-ene, propylene/butadiene, isobutylene/isoprene, ethylene-/alkyl acrylates, ethylene/alkyl methacrylates, ethylene/vinyl acetate copolymers and their copolymers with carbon monoxide or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE-/ethylene-vinyl acetate copolymers (EVA), LDPE/ethylene/acrylic acid copolymers (EAA), LLDPE/EVA, LLDPE/EAA and random or alternating polyalkylene/carbon monoxide-copolymers as well as mixtures thereof with other polymers, for example polyamides.

3a. Hydrocarbon resins (for example $C_5$-$C_9$) and hydrogenated modifications thereof (for example tackifiers) and mixtures of polyalkylenes and starch.

4. Polystyrene, poly(p-methylstyrene), poly($\alpha$-methylstyrene).

5. Copolymers of styrene or $\alpha$-methylstyrene with dienes or acrylic derivatives, such as, for example, styrene/butadiene, styrene/acrylonitrile, styrene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or $\alpha$-methylstyrene, for example styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed in 5), for example the copolymer mixtures known as ABS, MBS, ASA or AES polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, polymers of halogenated vinyl compounds, for example polyvinyl chloride, polyvinylidene chloride, polyvinyl fluoride, polyvinylidene fluoride, as well as copolymers thereof, for example vinyl chloride/- vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polymethyl methacrylate impact-modified with butyl acrylate, polyacrylamides and polyacrylonitriles.

9. Copolymers of the monomers mentioned in 8) with each other or with other unsaturated monomers, for example acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene and those polyoxymethylenes which contain ethylene oxide as comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes derived from polyethers, polyesters or polybutadienes with terminal hydroxyl groups on the one hand and aliphatic or aromatic polyisocyanates on the other, as well as precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6.12, 4/6, 12/12, polyamide 11, polyamide 12, aromatic polyamides obtained by condensation of m-xylene, diamine and adipic acid; polyamides prepared from hexamethylenediamine and isophthalic acid and/or terephthalic acid and optionally an elastomer as modifier, for example poly(2,4,4-trimethylhexamethylene) terephthalamide or poly-m-phenylene isophthalamide. Further copolymers of the aforementioned polyamides with polyolefins, olefin copolymers, ionomers or chemically bonded or grafted elastomers; or with polyethers, as with polyethylene glycols, polypropylene glycols or polytetramethylene glycols. Polyamides or copolyamides modified with EPDM or ABS. Polyamides condensed during processing (RIM polyamide systems).

16. Polyureas, polyimides, polyamide-imides and polybenzimidazoles.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, polyhydroxybenzoates as well as block-copolyether-esters derived from polyethers having hydroxyl end groups; and also polyesters which are modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other, such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents, and also halogenated modifications thereof of low inflammability.

23. Thermosetting acrylic resins derived from substituted acrylic esters, such as epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers, such as cellulose, rubber, gelatin and chemically modified homologous derivatives thereof, such as cellulose acetates, cellulose propionates and cellulose butyrates, or the cellulose ethers, such as methyl cellulose; rosins and their derivatives.

27. Mixtures of polymers as mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

Further objects of the invention are thus also compositions comprising an organic material which is subject to oxidative, thermal or light-induced degradation and at least one compound of formula (1).

Preferred organic materials are polymers, typically synthetic polymers, preferably thermoplastic polymers. Especially preferred are polyacetals or polyolefins such as polypropylene or polyethylene.

To be singled out for special mention is the efficacy of the novel compounds against thermal and oxidative degradation, especially under the action of heat which occurs during the processing of thermoplasts. The novel compounds therefore have outstanding utility as heat stabilisers.

The compounds of formula (1) will preferably be added to the organic material to be stabilised in concentrations of 5 to 50 000 ppm, most preferably of 10 to 20 000 ppm, based on the weight of said material.

In addition to comprising the compounds of formula (1), the inventive compositions may comprise further co-stabilisers, typically the following:

1. Antioxidants 1.1. Alkylated monophenols, for example 2,6-di-tert-butyl-4-methylphenol, 2-tert-butyl-4,6-dimethylphenol,2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-di-nonyl-4-methylphenol, 2,4-dimethyl-6-(1'-methyl-undec-1'-yl)phenol, 2,4-dimethyl-6-(1'-methyl-heptadec-1'-yl)phenol, 2,4-dimethyl-6-(1'-methyl-tridec-1'-yl)phenol and mixtures thereof.

1.2. Alkylthiomethylphenols, for example 2,4-dioctylthiomethyl-6-tert-butylphenol, 2,4-di-octylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2, 6-Di-tert-butyl-4-methoxyphenol, 2,5-di-tert-butyl-hydroquinone, 2,5-di-tert-amylhydroquinone, 2,6-diphenyl-4-octadecyloxyphenol, 2,6-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3, 5-di-tert-butyl-4-hydroxyphenyl)adipate.

1.4. Hydroxylated thiodiphenylethers, for example 2,2'-thiobis(6-tert-butyl-4-methylphenol), 2,2'-thiobis(4-octylphenol), 4,4'thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol) 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tertbutyl-4-hydroxy-2-methylphenyl)butane, 1,1-bis(5-tert-butyl-4-hydroxy-2-methylphenyl)3-n-dodecylmercaptobutane, ethylene glycol bis[3,3-bis(3'-tert-butyl-4'-hydroxyphenyl)butyrate], bis(3-tert-butyl-4-hydroxy-5-methylphenyl) dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O-, N- and S-benzyl compounds, for example 3,5,3',5'-tetra(tert-butyl-4,4'-dihydroxydibenzyl) ether, octadecyl-4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.7. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis-(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)2,3,5,6-tetramethylbenzene, 2,4,6-tris(3,5-di-tert-butyl-4-hydroxybenzyl)phenol.

1.9. Further Triazines, for example 2,4-bis[(octylmercapto-6-(3,5-di-tert-butyl-4-hydroxyanilino)]-1,3,5-triazine, 2-octylmercapto-4,6-bis(3,5-di-tert-butyl-4-hydroxyanilino)1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxbenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of monoethyl 3,5-di-tert-butyl-4-hydroxybenzylphosphonate.

1.11. Acylaminophenols, for example 4-hydroxylauryl anilide, 4-hydroxystearyl anilide, octyl N-(3,5-di-tertbutyl-4-hydroxyphenyl)carbamate.

1.12. Esters of β-(3,5-di-tertbutyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.13. Esters of β-(5-tert-butyl-4-hydroxy-3-methylphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.14. Esters of β-(3,5-dicyclohexyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis-(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis-(hydroxyethyl)oxalyl diamide, 3-triaundecanol, 3-thiapentadecanol, trimethylhexanediol, trimethylolpropane, 4-hydroxymethyl-1-phospha-2,6,7-trioxabicyclo[2.2.2]octane. 1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and light stabilisers 2.1. 2-(2'-Hydroxyphenyl)benzotriazoles, for example the 5'-methyl-,3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octyloxy-3',5'-di-tert-amyl- or 3',5'-bis(α,α-dimethylbenzyl)- mixture of 5-chloro-3'-tert-butyl-5'-(2-octyloxycarbonylethyl)-and 5-chloro-3'-tert-butyl-5'-[2-(2-ethylhexyloxy)-carbonylethyl]-, 5-chloro-3'-tert-butyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)-carbonylethyl]-, 3'-dodecyl-5'-methyl- and 3'-tert-butyl-5'-(2-isooctyloxycarbonylethyl)-2'-hydroxyphenyl-2H-benzotriazol-2-yl, 2,2'-methylenebis[4-(1,1,3,3-tetramethylbutyl)6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R-CH$_2$CH$_2$—COO(CH$_2$)$_3$]$_2$, wherein R=3'-tert-butyl-4'-hydroxy-5'-2H-benzotriazol-2-ylphenyl.

2.2. 2-Hydroxybenzophenonee, for example the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative.

2.3. Esters of unsubstituted or substituted benzoic acids, for example 4-tertbutylphenyl salicylate, phenyl salicylate, octylphenyl salicylate, dibenzoyl resorcinol, bis(4-tert-butylbenzoyl) resorcinol, benzoyl resorcinol, the 2,4-di-tertbutylphenyl ester of 3,5-di-tert-butyl-4-hydroxybenzoic acid, hexadecyl 3,5-di-tert-butyl-4-hydroxybenzoate, octadecyl 3,5-di-tert-butyl-4-hydroxybenzoate, the 2-methyl-4,6-di-tert-butylphenyl ester of 3,5-di-tert-butyl-4-hydroxybenzoic acid.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1- or 1:2 complex, with or without additional ligands, as n-butylamine, triethanolamine or N-cyclohexyl-diethanolamine, nickel dibutyl dithiocarbamate, nickel salts of monoalkyl esters of 4-hydroxy-3,5-di-tert-butylbenzylphosphonic acid, as of methyl or ethyl esters, nickel complexes of ketoximes, as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, the bis(1,2,2,6,6-pentamethylpiperidyl) ester of n-butyl-3,5-di-tert-butyl-4-hydroxybenzylmalonic acid, the condensate of 1-hydroxyethyl-2,2,6,6-tetramethyl-4-hydroxypiperidine and succinic acid, the condensate of N,N'-bis(2,2,6,6-tetramethyl-4-piperidyl)-hexamethylenediamine and 4-tertoctylamino-2,6-dichloro-1,3,5-s-triazine, tris(2,2,6,6-tetramethyl-4-piperidyl)-nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis-(3-aminopropylamino)ethane, the condensate of 2-chloro-4,6-di-(4-n-butylamino1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy4-dodecyloxyphenyl)-4,6-bis(2,4-dimethylphenyl)-1,3,5-triazine, 2-[2-hydroxy-4-(2-hydroxy-3-butoxy-propoxy)phenyl]-4,6-bis(2,4-dimethylphenyl)-1,3,5-triazine, 2-[2-hydroxy-4-(2-hydroxy-3-octyloxy-propoxy)-phenyl]-4,6-bis(2,4-dimethylphenyl)-1,3,5-triazine.

3. Metal deactivators, for example N,N'-diphenyloxamide, N-salicylal-N'-salicyloylhydrazine, N,N'-bis(-salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide, oxanilide, isophthalic dihydrazide, sebacic bis(phenylhydrazide), N,N'-diacetaladipic dihydrazide, N,N'-bis(-salicyloyl)oxalic dihydrazide, N,N'-bis(salicyloyl)thiopropionic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, bis(2,6-di-tert-butyl-4-methylphenyl)pentaerythritol diphosphite, bis(isodecyloxy)pentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine.

5. Compounds which decompose peroxide, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

The co-stabilisers are typically used in concentrations of 0.01 to 10%, based on the total weight of the material to be stabilised.

The compounds of formula (1), when used together with co-stabilisers such as phenolic antioxidants, exhibit a surprising synergistic effect during the stabilisation of polyacetal against thermal oxidative degradation.

The compounds of formula (1) and other optional additives are incorporated into the organic polymer by known methods, conveniently before or during shaping to moulded articles or alternatively by coating the organic polymers with a solution or dispersion of the compounds and subsequently evaporating the solvent. The compounds of formula (1) can also be added to the materials to be stabilised in the form of a masterbatch which contains these compounds, typically in a concentration of 2.5 to 25% by weight.

The compounds of formula (1) can also be added before or during polymerisation or before crosslinking.

The compounds of formula (1) can be incorporated into the organic polymer in pure form or in waxes, oils or polymer encapsulations.

The compounds of formula (1) can also be sprayed on to the polymer to be stabilised. They are able to dilute other additives (typically the conventional additives listed above) or melts thereof, so that they can also be sprayed together with these additives on to the polymer to be stabilised. Application by spraying during deactivation of the polymerisation catalysts is especially advantageous, in which case spraying is conveniently effected with the vapour used for deactivation.

It may be expedient to spray the compounds of formula (1), with or without other additives, on to spherical polymerised polyolefins.

A preferred embodiment of this invention is therefore the use of compounds of formula (1) for stabilising polymers against oxidative, thermal and/or light-induced degradation by spraying said compounds on to the polymer.

The stabilised materials may be in any form of presentation, typically sheets, filaments, ribbons, mouldings, profiles or binders for coating compositions, adhesives or putties.

As already emphasised, the novel compounds are used with particular advantage as stabilisers in polyolefins, preferably as heat stabilisers. Excellent stabilisation is achieved when the compounds are used in conjunction with organic phosphites or phosphonites. The novel compounds have in this case the advantage that they are effective in exceedingly low concentration, typically of 0.0001 to 0.015% by weight, preferably of 0.0001 to 0.008% by weight, based on the polyolefin. The organic phosphite or phosphonite is conveniently used in a concentration of 0.01 to 2% by weight, preferably of 0.01 to 1% by weight, based on the polyolefin. It is preferred to use the organic phosphites and phosphonites disclosed in German patent application P 4202276.2. Attention is drawn in particular to the claims, to the Examples and to pages 5, last paragraph, to 11. Particularly suitable phosphites and phosphonites will also be found under item 4 of the above list of co-stabilisers.

The invention is illustrated in more detail by the following Examples in which parts and percentages are by weight.

PREPARATION OF THE COMPOUNDS OF FORMULA (1)

Example 1

76.1 g (0.2 mol) of 1,1-bis(3-tert-butyl-4-hydroxyphenyl)cyclohexane are mixed with 36.5 g (0.24 mol) of mandelic acid, and the mixture is then stirred for 4.75 hours at 200° C. and c. 50 torr. Then another 36.5 g (0.24 mol) of mandelic acid are added and the mixture is stirred under the same conditions for a further 16.75 hours. Afterwards the temperature is lowered. Then 20 ml of toluene and 300 ml of methanol are added through a reflux condenser and stirring is continued for another 4 hours, finally at room temperature. The precipitated crystals are collected by suction filtration, washed with methanol and dried, giving 79 g (0.129 mol, 65%) of compound (105) listed in Table 1 with a melting point of 205°–208° C.

TABLE 1

| No. | Compound | m.p. (°C.) | C (%), H (%) (calcd./found) | Yield (%) |
|---|---|---|---|---|
| 101 | (structure shown) | 80–88 | 81.46  5.39<br>81.31  5.29 | 26 |

TABLE 1-continued

| No. | Compound | m.p. (°C.) | C (%), H (%) (calcd./found) | Yield (%) |
|---|---|---|---|---|
| 102 | | 90–105 | 81.58  5.64<br>81.30  5.56 | 53 |
| 103 | | 85–105 | 81.79  6.10<br>81.91  6.39 | 45 |
| 104 | | 142–152 | 82.16  6.90<br>82.29  7.02 | 31 |
| 105 | | 205–208 | 82.32  7.24<br>82.10  7.26 | 65 |
| 106 | | 140–148 | 82.32  7.24<br>82.36  7.31 | 31 |
| 107 | | 200–223 | 83.10  7.28<br>82.60  7.31 | 63 |

TABLE 1-continued

| No. | Compound | m.p. (°C.) | C (%), H (%) (calcd./found) | Yield (%) |
|---|---|---|---|---|
| 108 | | 188-194 | 82.39 7.40<br>82.23 7.36 | 47 |
| 109 | | 173-176 | 82.60 7.84<br>82.56 7.74 | 31 |
| 110 | | 195-203 | 82.39 7.40<br>82.33 7.42 | 53 |
| 111 | | 250-257 | characterised by MS: for $C_{46}H_{52}O_4$ found $M^+ = 668$ | 78 |
| 112 | | 224-226 | 78.54 7.19<br>78.26 7.23 | 70 |

TABLE 1-continued

| No. | Compound | m.p. (°C.) | C (%), H (%) (calcd./found) | Yield (%) |
|---|---|---|---|---|
| 113 | | 187–190 | 79.09  7.74<br>78.88  7.71 | 55 |
| 114 | | 140–155 | characterised by MS:<br>for C$_{46}$H$_{52}$O$_6$<br>found M$^+$ = 700 | 99 (crude) |
| 115 | | 130–150 | 76.74  8.11<br>77.23  8.01 | 35 |
| 116 | | 210–213 | 78.83  7.48<br>78.70  7.70 | 80 |

TABLE 1-continued

| No. | Compound | m.p. (°C.) | C (%), H (%) (calcd./found) | Yield (%) |
|---|---|---|---|---|
| 117 | | 215-227 | 75.41 6.33<br>75.35 6.29 | 43 |
| 118 | | 180-193 | 79.76 7.50<br>79.78 7.60 | 70 |
| 119 | | 93-98 | FAB MS:<br>for $C_{56}H_{56}O_6$<br>found $M^+ = 825$ | 60 |
| 120 | | resin* | *isolated by chromatography on silica gel with hexane/ethyl acetate 9:1<br>79.33 7.99<br>79.05 8.06 | 18 |

TABLE 1-continued

| No. | Compound | m.p. (°C.) | C (%), H (%) (calcd./found) | Yield (%) |
|---|---|---|---|---|
| 121 | (structure: bis-phenolic compound with two CH₃–C(CH₃)–CH₃ (tert-butyl) groups, cyclohexylidene linker, and two –O–C₁₆H₃₃ groups) | resin* | **isolated by chromatography on silica gel with CH₂Cl₂/hexane = 1:1<br>81.27  9.95<br>       10.03 | 50 |
| 122 | (structure: bis-phenolic compound with trimethylcyclohexylidene linker and two –OCH₂CH₃ groups) | 150–154 | 78.07  6.71<br>77.95  6.74 | 20 |

Compounds 101) to (104) and (106) to (110) can be prepared in accordance with the general procedure described in Example 1.

Example 2

57.0 g of bis(3-tert-butyl-4-hydroxyphenyl)cyclohexane are mixed with 34.65 g of 3,5-dimethyl-4-methoxymandelic acid and 100 ml of toluene, and the mixture is heated to reflux with stirring. The toluene is then removed by distillation and the temperature is raised to 180° C. The residue is thereafter stirred for 1 hour at 180° C. under a vacuum of c. 100 mbar. Then another 34.65 g of 3,5-dimethyl-4-methoxymandelic acid are added and the batch is stirred for 4.5 hours at 180° C. under vacuum. To the no longer heated and warm reaction mixture are cautiously added 25 ml of xylene and then 250 ml of methanol. The resultant solution is slowly cooled, with stirring, to 5° C., whereupon compound (113) crystallises. The product is isolated by filtration, washed with methanol and dried, giving 88.2 g of compound (113) in Table 1, m.p. 187°–190° C.

Following the general procedure of Example 2, compounds (111), (112), (116), (117), (118), (119), (120), (121) and (122) are prepared from the appropriate mandelic acids.

Example 3

0.76 g of bis(3-tert-butyl-4-hydroxyphenyl)cyclohexane and 0.80 g of 3,5-dimethyl-4-hydroxymandelic acid are dissolved at 75° C. in 10 ml of acetic acid. Then 0.2 ml of concentrated sulfuric acid is added and the batch is stirred for 2.75 hours at 75° C. Then 10 ml of water are added to the reaction mixture and the precipitate is collected by suction filtration, washed with water and dried, giving 1.4 g of compound (114) in Table 1, m.p. 140°–155° C.

Compound (115) is obtained from compound (114) by known acylation with pivalyl chloride.

Example 4

Stabilisation of the melt index of multiple-extruded polypropylene 1.3 kg of polypropylene powder (melt index 3.2 g/10 min, measured at 230° C./2.16 kg) are blended with 0.05% of Irganox ® 1010 (pentaerythritol tetrakis[3-(3,5-di-tert-butyl-4-hydroxyphenyl)propionate), 0.05% of calcium stearate, 0.03% of dihydrotalcite and 0.01% of processing stabiliser. This blend is then extruded in an extruder having a cylinder diameter of 20 mm and a length of 400 mm at 100 rpm, the 3 heating zones being adjusted to the following temperatures: 260°, 270°, 280° C. The extrudate is cooled by drawing it through a water bath and is then granulated. This granulate is repeatedly extruded. After 3 and after 5 extrusions, the melt index is measured (at 230° C./2.16 kg). A substantial increase in the melt index denotes pronounced chain degradation, i.e. poor stabilisation. The results are shown in Table 2.

TABLE 2

| Compound | Melt index after 5 extrusions | Melt index after 3 extrusions |
|---|---|---|
| none | 27 | 20 |
| 104 | 9.4 | |
| 105 | 10.5 | |
| 107 | 10 | |
| 108 | 12.6 | |
| 109 | 9.3 | |
| 110 | 9.5 | |
| 112 | | 5.7 |
| 113 | | 6.0 |
| 116 | | 5.9 |
| 118 | | 4.1 |

Example 5

Stabilisation of polyacetal against thermal oxidative degradation 100 parts of polyacetal powder are blended with 0.3 part of calcium stearate and 0.3 part of stabiliser. The blend is then kneaded in a Brabender plastograph for 7 minutes at 190° C./30 rpm. The kneading stock is compressed to 1 mm boards from which 27 mg test specimens are punched. The specimens are heated in a TGA to 220° C. under nitrogen. Nitrogen is then replaced with air and the onset of the decrease in weight attributable to oxidative degradation of the test specimens is recorded as a function of the time. The time taken until a 10% decrease in weight is reached is taken as a measure of the stabilising action. The longer this time is, the more effective is the stabiliser. The results are summarised in Table 3.

TABLE 3

| Compound | Time taken until 10% decrease in weight (min) |
|---|---|
| none | c. 10 seconds |
| 105 | 62.8 |
| 107 | 72.3 |
| 108 | 71.7 |

Example 6

Synergism between the novel compounds and a phenolic antioxidant [Irganox ® 245 (triethylene glycol bis[3-(3,5-di-tert-butyl-4-hydroxyphenyl)propionate]) and Irganox ® 1010 (pentaerythritol tetrakis[3-(3,5-di-tert-butyl-4-hydroxyphenyl)propionate)] during the stabilisation of polyacetal against thermal oxidative degradation.

A) Without addition of melamine 100 parts of polyacetal powder are blended with 0.3 part of calcium stearate, 0.3 part of the phenolic antioxidant listed in Table 4 and 0.05 part of novel stabiliser. The blend is then kneaded in a Brabender plastograph for 7 minutes at 190° C./30 rpm. The kneading stock is compressed to 1 mm boards from which 27 mg test specimens are punched. The specimens are heated in a TGA to 220° C. under nitrogen. Nitrogen is then replaced with air and the onset of the decrease in weight attributable to oxidative degradation of the test specimens is recorded as a function of the time. The time taken to reach a 10% decrease in weight is taken as a measure of the stabilising action. The longer this time is, the more effective is the stabiliser. The results are summarised in Table 4.

TABLE 4

| Compound | Time taken until 10% decrease in weight (min) |
|---|---|
| 0.3 part of Irganox 245 | 43 |
| 0.3 part of Iganox 1010 | 39 |
| 0.05 part of compound 105 | ~7 |
| 0.05 part of compound 108 | ~7 |
| Irganox 245/ compound 105 | 60 |
| Irganox 245/ compound 108 | 62 |
| Irganox 1010/ compound 105 | 69 |
| Irganox 1010/ compound 108 | 74 |

B) With addition of melamine

A test series similar to that in A) is run, except that the test blend additionally contains 0.1 part of melamine. The results are summarised in Table 5.

TABLE 5

| Compound | Time taken until 10% Decrease in weight (min) |
|---|---|
| 0.3 part of Irganox 1010 | 94 |
| 0.05 part of compound 112, 113 or 116 | ~5 |
| Irganox 1010/ compound 112 | 125 |
| Irganox 1010/ compound 113 | 115 |
| Irganox 1010/ compound 116 | 115 |

What is claimed is:

1. A compound of formula (1)

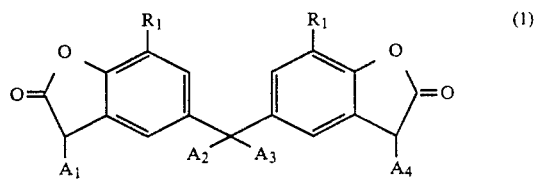

wherein $R_1$ is hydrogen, $C_1$-$C_8$alkyl, $C_5$-$C_8$cycloalkyl or $C_7$-$C_9$phenylalkyl, $A_1$ and $A_4$ are phenyl,

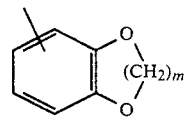

or phenyl which is substituted by 1 to 3 radicals $R_3$, which radicals $R_3$ are each independently of one another selected from the group consisting of $C_1$-$C_4$alkyl, $C_1$-$C_{18}$alkoxy, $C_3$-$C_4$alkenyloxy, $C_7$-$C_9$phenylalkoxy, $C_5$-$C_8$cycloalkoxy, $C_1$-$C_{18}$alkenoyloxy, $C_3$-$C_{18}$alkenoyloxy, benzoyloxy, phenoxy and hydroxy, m is 1 or 2, $A_2$ and $A_3$, together with the linking carbon atom, form a $C_5$-$C_7$cycloalkylidene ring which is unsubstituted or substituted by 1 to 3 $C_1$-$C_4$alkyl groups.

2. A compound according to claim 1, wherein $R_1$ is hydrogen, $C_1$-$C_8$alkyl or $C_5$-$C_8$cycloalkyl, $A_1$ and $A_4$ are phenyl, $A_2$ and $A_3$ together form a group

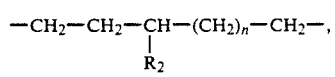

wherein, if n is 1, $R_2$ is hydrogen or $C_1$-$C_4$alkyl and, if n is 0 or 2, $R_2$ is hydrogen.

3. A compound according to claim 1, wherein $R_1$ is hydrogen, $C_1$-$C_4$alkyl or cyclohexyl.

4. A compound according to claim 1, wherein $R_1$ is tert-butyl and $A_2$ and $A_3$ together are a group

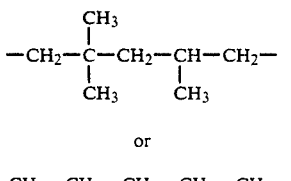

or $-CH_2-CH_2-CH_2-CH_2-CH_2-$.

5. A compound according to claim 1, wherein $A_1$ and $A_4$ are phenyl or phenyl which is substituted by 1 to 3 radicals $R_3$, which radicals $R_3$ are each independently of one another selected from the group consisting of $C_1$-$C_4$alkyl, $C_1$-$C_{18}$alkoxy, benzoxy, $C_1$-$C_{18}$alkanoyloxy, benzoyloxy and hydroxy.

6. A compound according to claim 1, wherein $A_1$ and $A_4$ are

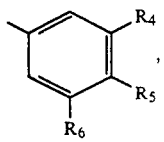

wherein $R_4$ and $R_6$ are each independently of the other hydrogen or $C_1$-$C_4$alkyl, and $R_5$ is hydroxy, $C_1$-$C_{18}$alkoxy, $C_1$-$C_{18}$alkanoyloxy or benzoxy.

7. A compound according to claim 1, wherein $R_1$ is hydrogen, $C_1$-$C_4$alkyl or cyclohexyl, $A_1$ and $A_4$ are phenyl,

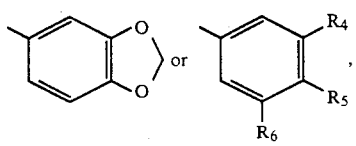

wherein $R_4$ and $R_6$ are each independently of the other hydrogen or methyl, and $R_5$ is hydroxy, $C_1$-$C_{18}$alkoxy, methyl, $C_1$-$C_8$alkanoyloxy or benzoxy, $A_2$ and $A_3$, together with the linking carbon atom, form a $C_5$-$C_7$cycloalkylidene ring, or $A_2$ and $A_3$ together are a group

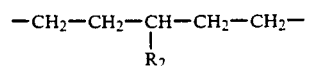

or

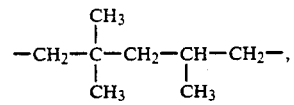

wherein $R_2$ is methyl or tert-butyl.

8. A composition comprising
a) an organic material which is subject to oxidative, thermal or light-induced degradation, and
b) at least one compound according to claim 1 which is present in an amount sufficient to inhibit said degradation.

9. A composition according to claim 8, wherein component a) is a synthetic polymer.

10. A composition according to claim 8, which contains 5 to 50 000 ppm of component b), based on the weight of component a).

11. A composition according to claim 8, which additionally comprises an organic phosphite.

12. A composition according to claim 8, which additionally comprises a phenolic antioxidant.

13. A process for stabilising an organic material against oxidative, thermal or light-induced degradation, which comprises incorporating therein at least one compound as claimed in claim 1.

* * * * *